(12) United States Patent
Yoon (10) Patent No.: US 6,277,064 B1
(45) Date of Patent: Aug. 21, 2001

(54) SURGICAL INSTRUMENT WITH ROTATABLY MOUNTED OFFSET ENDOSCOPE

(76) Inventor: InBae Yoon, 2101 Highland Ridge Dr., Phoenix, MD (US) 21131

( * ) Notice: Subject to any disclaimer, the term of this patent is extended or adjusted under 35 U.S.C. 154(b) by 0 days.

(21) Appl. No.: 09/222,703

(22) Filed: Dec. 29, 1998

Related U.S. Application Data (60) Provisional application No. 60/070,196, filed on Dec. 30, 1997.

(51) Int. Cl.[7] ............................... A61B 1/00; A61B 1/018
(52) U.S. Cl. ......................... 600/114; 600/104; 600/129; 600/138; 600/171; 600/173
(58) Field of Search ................................... 600/102, 104, 600/105, 106, 111, 113, 114, 129, 130, 137, 160, 166, 171, 173

(56) References Cited

U.S. PATENT DOCUMENTS

| | | |
|---|---|---|
| 2,580,964 | 1/1952 | Skaller . |
| 3,918,439 * | 11/1975 | Zimmer ................. 600/104 |
| 4,635,638 | 1/1987 | Weintraub . |
| 5,222,508 | 6/1993 | Contarini . |
| 5,308,353 | 5/1994 | Beurrier . |
| 5,351,678 * | 10/1994 | Clayton et al. ............... 600/114 |
| 5,368,015 * | 11/1994 | Wilk ......................... 600/166 |
| 5,538,497 * | 7/1996 | Hori ......................... 600/166 |
| 5,607,435 * | 3/1997 | Sachdeva et al. ............. 600/139 |
| 5,924,976 * | 7/1999 | Stelzer et al. ............... 600/106 |
| 5,928,137 * | 7/1999 | Green ....................... 600/160 |

FOREIGN PATENT DOCUMENTS

WO97/37583   10/1997 (WO) ................. A61B/1/00

* cited by examiner

*Primary Examiner*—John P. Leubecker
(74) *Attorney, Agent, or Firm*—Blank Rome Comisky & McCauley LLP (57) ABSTRACT

A surgical endoscopic instrument for operating on anatomical tissue includes a rigid barrel, a shaft extending through the barrel and an offset endoscope mounted on the shaft. The endoscope is offset from the longitudinal axis of the shaft by a transverse connecting member, thereby permitting the endoscope viewing end to move through an arcuate path outside the diametrical dimension of the barrel. During insertion of the instrument through a portal or the like, the offset endoscope can be positioned within a diametrical dimension of the surgical instrument, either by rotating the shaft or by drawing the shaft and the endoscope viewing end into the barrel in an axial manner. The offset endoscope may be aimed to provide an oblique field of view of a surgical procedure and may include an articulable ball joint having a solid state imaging sensor and light source; the ball joint imaging sensor aim is preferably articulable or controllable from the instrument proximal end using control members (e.g., wires) connected to handle-mounted control wheels. In an alternative embodiment, the offset endoscope has a fixed objective lens carried on the distal end of a rigid tubular body carried on a transverse connecting member. The fixed objective lens is preferably angled to aim along the transverse offset axis and generally toward the endoscopic instrument axis, to provide an oblique field of view of other surgical instruments used in other channels.

14 Claims, 5 Drawing Sheets

SURGICAL INSTRUMENT WITH ROTATABLY MOUNTED OFFSET ENDOSCOPE

RELATED APPLICATION DATA

This application claims benefit of provisional application No. 60/070,196 filed Dec 30, 1997.

This application is related to applicant's applications 08/847,252, now U.S. Pat. Nos. 6,080,180, and 08/847,254, now U.S. Pat. No. 6,004,332, both filed May 1, 1997, and 08/877,764 filed Jun. 17, 1997, now U.S. Pat. No. 5,993,466, the entire disclosures of which are incorporated herein by reference.

BACKGROUND OF THE INVENTION

1. Field of the Invention

The present invention pertains to an apparatus and method for endoscopic and open surgery and, more particularly, to a surgical device incorporating a rigid endoscopic instrument and methods of manipulating the endoscope.

2. Discussion of the Prior Art

Various procedures are accomplished in both open surgery and endoscopic surgery, and generally, the procedures include multiple steps and require various operating instruments. "Open surgery" refers to surgery wherein the surgeon gains access to the surgical site by a relatively large incision and "endoscopic surgery" refers to minimally invasive surgery wherein the surgeon gains access to the surgical site via one or more portals through which endoscopes are introduced to view the surgical site and through which instruments having "end effectors", such as forceps, cutters, needle holders, cauterizers, and the like, are introduced to the surgical site.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn, leaving the sleeve in place to form a portal in the cavity wall for the introduction of instruments such an endoscopes, scissors, forceps, needle holders and the like, into the anatomical cavity.

The various end effectors at the distal end of the instrument are manipulated by the surgeon using controls disposed at the proximal end of the instrument. Of course, it is desirable to move the end effectors through various paths, depending on the step being performed. Traditionally, this was accomplished by moving the entire end of the endoscopic instrument. Recently, however, it has been proposed to provide a plurality of end effectors on a single endoscopic instrument to be passed through a single portal for minimizing the number of puncture sites and thus reducing the risk and the healing time associated with endoscopic surgery.

When a plurality of end effectors are incorporated into a single endoscopic device, it is desirable to move the end effectors individually with respect to one another without necessarily moving the entire device. Also, even in single end effector devices, it is often desirable to move the end effector through a predetermined path, such as an arc, during an operative step, without repositioning the entire endoscopic device.

Of course, it is also generally desirable to minimize the size of each puncture site. Further, in order to permit operations on a wide range of tissue sizes, it is desirable to provide a wide range of relative movement between the end effectors. The objectives, minimal number of punctures, small size punctures and wide range of relative movement, are seemingly contradictory and so conventional devices of the prior art have not achieved them.

In particular, U.S. Pat. No. 5,582,617 discloses an endoscopic instrument having an end effector movable from a position within the diameter of the barrel of the device to a position outside the diameter. However, this device must pivot about a first axis transverse to the axis of the barrel as well as a second axis coincident with the axis of the barrel and thus requires a complex movement and linkage to accomplish the disclosed functions. Accordingly, the device of the '617 patent falls short of providing an end effector for utilization over a large working span and for a wide range of applications. A surgical instrument with a rotatably mounted offset end effector, as disclosed in applicant's own U.S. patent application Ser. No. 08/847,252, discussed above, provides an important advance in permitting surgeons to perform such complex movements, over a large working span, and permitting multiple offset end effectors to be used. A problem associated with using multiple offset end effectors in a traditional endoscope having fixed point of view at the distal end of a rigid instrument is that the offset end effectors may swing into a position away from or blocking the endoscope view. This is especially troublesome in situations involving multiple end effectors used simultaneously. In such cases, the prior art endoscope provides a straight-on view from behind the end effectors and so cannot be used to directly view the entire end effector during a procedure, and so there is a need for a mechanism and method allowing visibility when using surgical instruments having rotatably mounted offset end effectors as disclosed in application Ser. No. 08/847,252.

OBJECTS AND SUMMARY OF THE INVENTION

Accordingly, it is a primary object of the present invention to overcome the above-mentioned problems and to improve surgical instruments and methods of endoscopic surgery.

It is also an object of the invention to provide an endoscopic device having a small insertion diameter and providing an oblique field of view of offset end effectors having large working spans.

Yet another object of the present invention is to minimize the number of puncture sites required for performing operative steps on anatomical tissue in an endoscopic procedure by conducting multiple procedures through a single puncture site with an instrument providing acceptable visibility to the surgeon, while moving an offset end effector through a predetermined path to operate on the anatomical tissue.

The aforesaid objects are achieved individually and in combination, and it is not intended that the present invention be construed as requiring two or more of the objects to be combined unless expressly required by the claims attached hereto.

The present invention is generally characterized in an instrument for operating on anatomical tissue including a tubular barrel, a shaft extending through the barrel and an offset endoscope mounted on the shaft. The offset endoscope viewing end is laterally offset from the longitudinal axis of the shaft by a transverse connecting member, thereby permitting the endoscope viewing end to move through an arcuate path outside the diametrical dimension of the barrel. During insertion of the surgical instrument within a portal sleeve or the like, the offset endoscope can be positioned within a diametrical dimension of the surgical instrument, either by rotating the shaft (e.g., rotating the endoscope body to angularly position the viewing end so as to lie within a circle having the outer diameter of the barrel) or by drawing the shaft and the endoscope viewing end into the barrel, in an axial manner.

The offset endoscope may be aimed to provide an oblique field of view of the procedure and may include an articulable ball joint having a solid state imaging sensor and light source; the ball joint imaging sensor aim is preferably articulable or controllable from the instrument proximal end using control members (e.g., wires) connected to handle-mounted control wheels (as disclosed in FIG. 19 of Applicant's U.S. Pat. No. 5,437,680, the entire disclosure of which is incorporated herein by reference).

In an alternative embodiment, the offset endoscope has a fixed objective lens carried on the distal end of a rigid tubular body having a transverse connecting member. The fixed objective lens is preferably angled to aim along the transverse offset axis and generally toward the endoscopic instrument barrel central axis, to provide an oblique field of view of other surgical instruments used in other channels.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 1a is a perspective illustration of a surgical instrument including an offset endoscope.

FIG. 1b is an enlarged view of the proximal end of offset endoscope of FIG. 1a.

FIGS. 7a, 7b, 7c and 7d are distal end views, in elevation, illustrating the range of motion of the offset endoscope of FIG. 1a.

DESCRIPTION OF THE PREFERRED EMBODIMENT

Figures 1A, 1B:
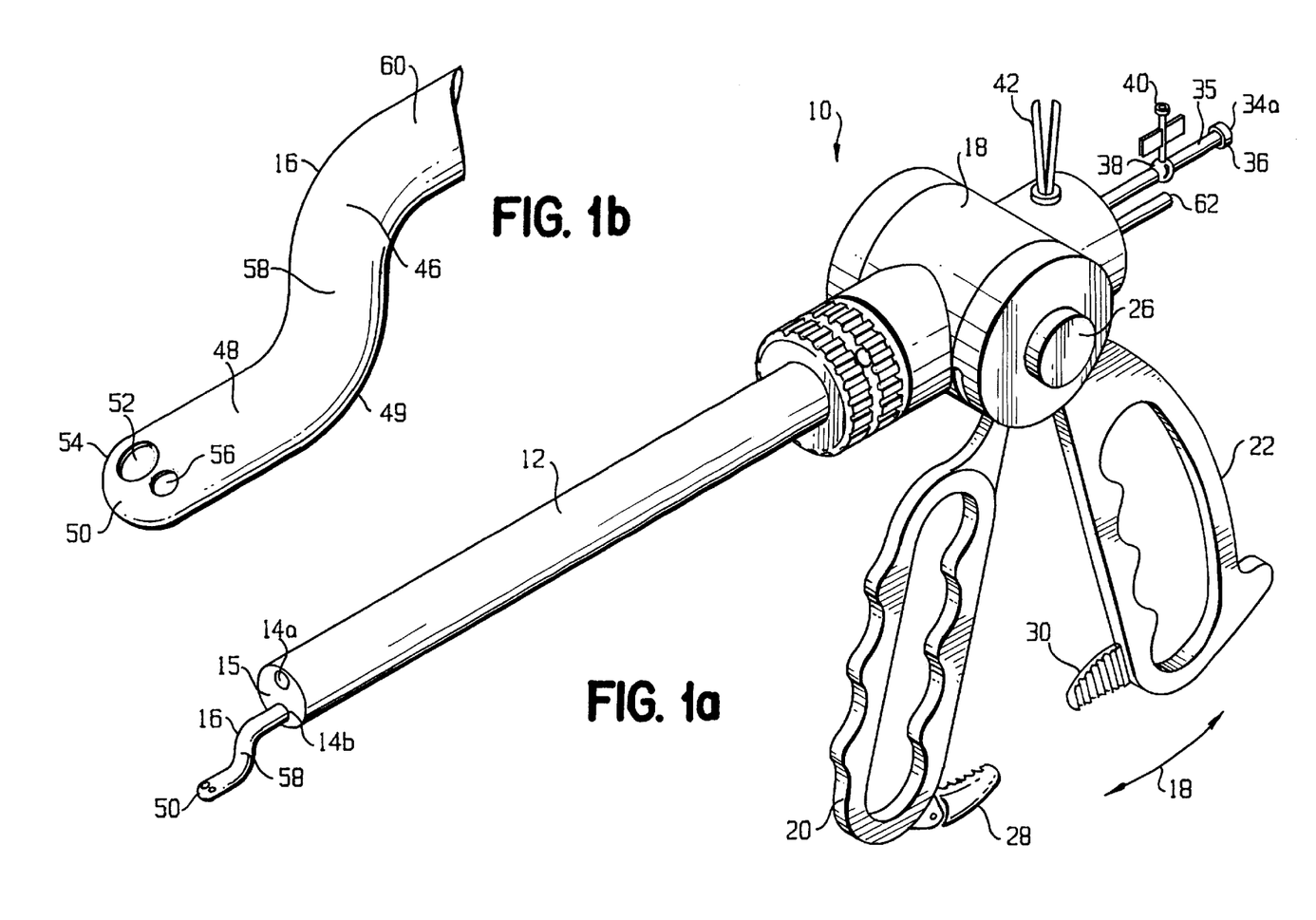
Figures 2, 3, 9:
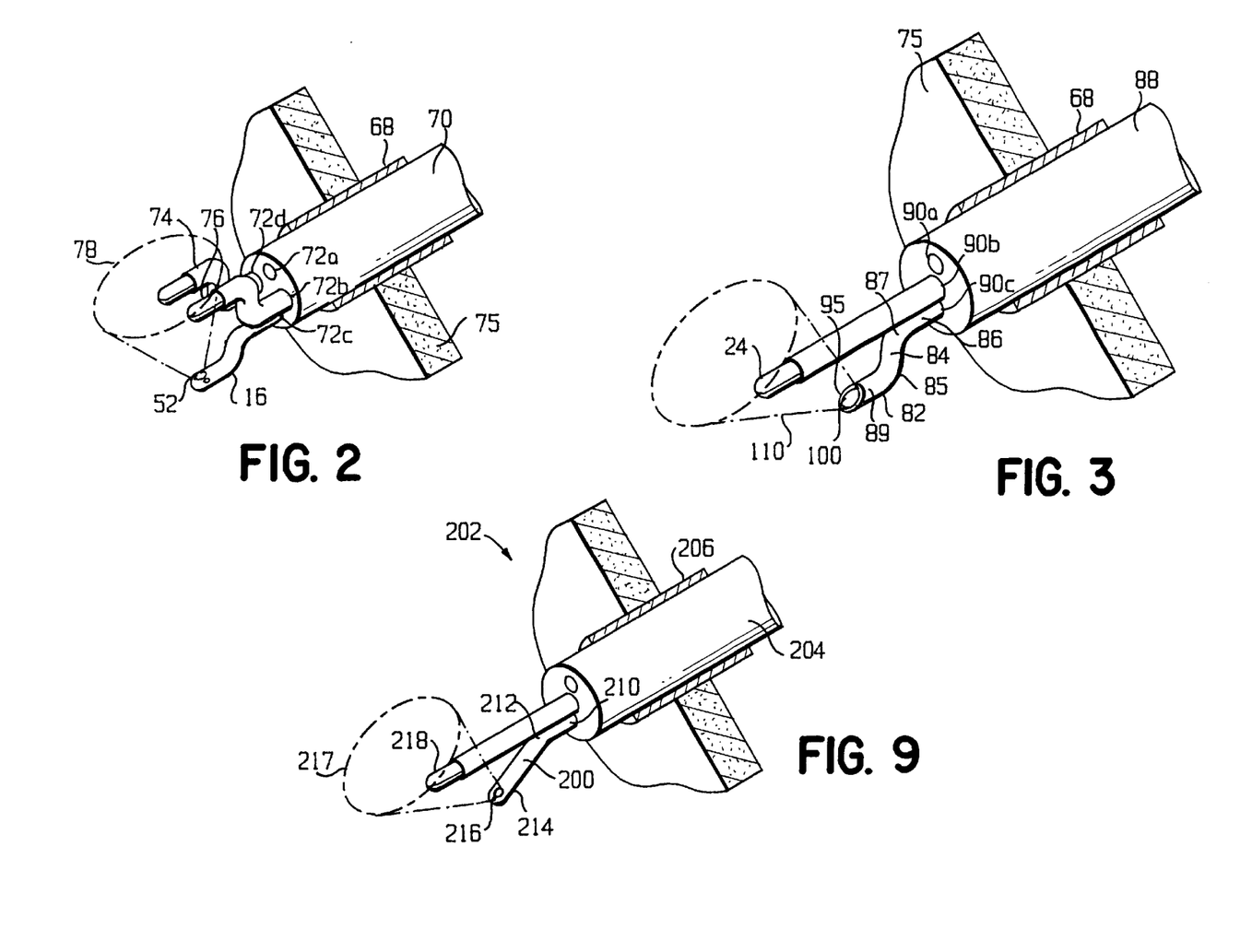
FIG. 2 is a perspective illustration, in partial cross section, illustrating deployment of an offset endoscope after insertion through a portal, in the body.
FIG. 3 is a perspective illustration, in partial cross section, showing an alternative embodiment of the offset endoscope.
FIG. 9 is a perspective view of an alternative embodiment of the offset endoscope.

In accordance with the present invention, as illustrated in FIGS. 1a and 1b, a surgical instrument 10 can be used to visualize any type of anatomical tissue in any type of anatomical cavity. While the instrument 10 is described hereinafter for use with a tubular portal sleeve 68 (as best seen in FIGS. 2 and 3) in endoscopic procedures, such as laparoscopy, the instrument can be used in open surgery and with catheters and other small and large diameter tubular or hollow cylindrical members providing access to small cavities, such as veins and arteries, as well as large cavities, such as the abdomen.

The endoscopic instrument according to a first preferred embodiment of the present invention is illustrated in FIGS. 1a and 1b and includes a cylindrical barrel, or outer shaft 12 having an elongated passage defined therein (preferably in the form of one or more channels, e.g., 14a and 14b), a barrel distal end 15 and a barrel proximal end terminating in a housing 18. Housing 18 includes scissor type handles 20 and 22 for controlling surgical instruments such as end effectors having jaw members 24 (as best seen in FIG. 3), or the like. Housing 18 also includes a transversely located button 26 for selectively disengaging the scissor type handles 20 and 22 and permitting rotation of the handles about the axis of rotation indicated by the arrow A in FIG. 1a. This allows the surgeon to orient handles 20 and 22 in a desired manner before or during surgery. The handles 20 and 22 also include serrated lock protrusions 28 and 30 to interlock and allow the position of handles 20 and 22 to be maintained in a state corresponding to a desired position of the end effectors. Lock protrusions 28 and 30 can be pivoted to a position to prevent interlock, if desired. Handles 20 and 22 are configured to be grasped while the surgeon's fingers pass through the openings in the handles or while the surgeon's fingers are wrapped around the outer portions of the handles, to increase comfort and adaptability.

The channels (e.g., 14a and 14b) in barrel 12 are lumens or passages adapted to receive elongate surgical instruments which can be inserted at the proximal ends of the channels (e.g., proximal end 34a); channel 14a extends through proximal tubular body 35, which carries a Luer lock 36 and a spherical reservoir 38 for receiving a stop-cock valve 40, thereby allowing channel 14a to be sealed at the proximal end. Housing 18 includes a cautery electrode connection 42 for removable electrical connection to a source of electrical energy for cauterizing tissue using end effectors (e.g., forceps jaws 24 as illustrated in FIG. 3).

As illustrated in FIGS. 1a and 1b, an offset endoscope 16 has an elongate, rigid tubular body 60 with longitudinal axis and a distal end 46 opposite a proximal end 62 and is adapted to be slidably received within a barrel channel (e.g., 14b). The offset endoscope 16 has a rigid transverse connecting member 58 rigidly connected to and extending laterally from the distal end 46, providing an offset of a selected transverse dimension. In the embodiment of FIGS. 1 and 1a, a longitudinally aligned distal member 48 is carried on the lateral end 49 of transverse connecting member 58 and is terminated in offset endoscope distal end 50.

In proximity to offset endoscope distal end 50, an image receiving element 52 gathers light to form an image which the surgeon can interpret in performing endoscopic procedures. Image receiving element 52 can be an objective lens and/or the distal end of a fiberoptic bundle extending to the endoscope proximal end, or an objective lens focusing an image onto a light sensing device such as a CMOS or CCD imaging array or a vidicon, for transmitting image signals out of the body for viewing.

The offset endoscope 16 preferably also includes one or more light sources 54 and 56 for illuminating the field of view observable through the image receiving element 52. The offset endoscope light source may be a light emitting diode (LED) or the distal end of a fiberoptic bundle or series of lenses used in conjunction with a light guide for transmitting light from the proximal end of instrument 10 to the light source (e.g., 54 and 56) located proximate the distal end 50. The optical endoscope rigid transverse connecting member 58 provides a fixed offset of a selected transverse dimension for positioning the offset endoscope image receiving element 52 to receive an oblique view of end effectors (e.g., jaws 24 as in FIG. 3) during endoscopic surgery.

As is best seen in FIG. 2, a surgical instrument in accordance with the present invention can include a barrel 70 having four channels 72a, 72b, 72c and 72d adapted to accommodate offset endoscope 16 and offset forceps or needle holder instruments (or drivers) 74 and 76, all of which are insertable through portal sleeve 68 providing a portal into the body through anatomical wall 75. The offset endoscope image receiving element 52 has an oblique field of view 78 including a view of the distal ends and sides of offset needle holders 74 and 76. Oblique field of view 78 is disposed at an angle between 0° and 180° with respect to the longitudinal axis of barrel 70. In the embodiment of FIG. 2, the oblique field of view 78 includes a solid angle having a radius of approximately 30° and centered at an angle between 60° and 80° from the longitudinal axis of barrel 70. As can be seen from inspection of FIG. 2, the oblique field of view 70 corresponds to an aim point for image receiving element 52 directed along the transverse axis of transverse connection member 58. Thus, as offset endoscope 16 is rotated about the longitudinal axis of channel 72c, the oblique field of view 78 can be altered to view offset needle holders 74 and 76 from a variety of angles or perspectives.

Offset endoscope 16 is slidably received in channel 72c and may be moved axially in proximal or distal directions and is rotatable therein for providing an infinite number of viewing perspectives. Offset endoscope image receiving element 52 can thus be moved radially along an arc centered on the longitudinal axis of offset endoscope rigid tubular body 60, disposed coaxially with channel 72c.

Turning now to FIG. 3, there is illustrated an alternative embodiment of an offset endoscope 82 having a transverse connecting member 84 connected to a rigid tubular body 86. In the embodiment of FIG. 3, instrument barrel 88 includes three channels therethrough, 90a, 90b and 90c. Offset endoscope 82 includes an image receiving element 100 which can comprise an objective lens or the distal end of a bundle of fiber optic elements, or the like, as above. More particularly, offset endoscope 82 has an elongate, rigid tubular body 86 having a longitudinal axis and a distal end 87 opposite a proximal end (not shown) and is adapted to be slidably received within a barrel channel (e.g., 90c). The offset endoscope 86 has rigid transverse connecting member 84 rigidly connected to and extending laterally from the distal end 87, providing an offset of a selected transverse dimension. In the embodiment of FIG. 3, a longitudinally aligned distal member 89 is carried on the lateral end 85 of transverse connecting member 84 and is terminated in an offset endoscope distal end having an end face 95 disposed at an oblique angle to the longitudinal axis of offset endoscope tubular body and including image receiving element 100.

A light source is integrated into offset endoscope 82 and shines outwardly from the end face 95 illuminating at least a region having the same solid angle as the oblique field of view 110, as shown in FIG. 3. The end effector 24 can be advanced distally or withdrawn proximally and the offset endoscope can also be advanced distally, withdrawn proximally and/or rotated within channel 90c, to provide a variety of oblique viewing perspectives of the jaws of end effector 24. Optionally, a second offset endoscope can be carried in channel 90a to provide simultaneous oblique views of a surgical procedure or the like.

Figure 4:
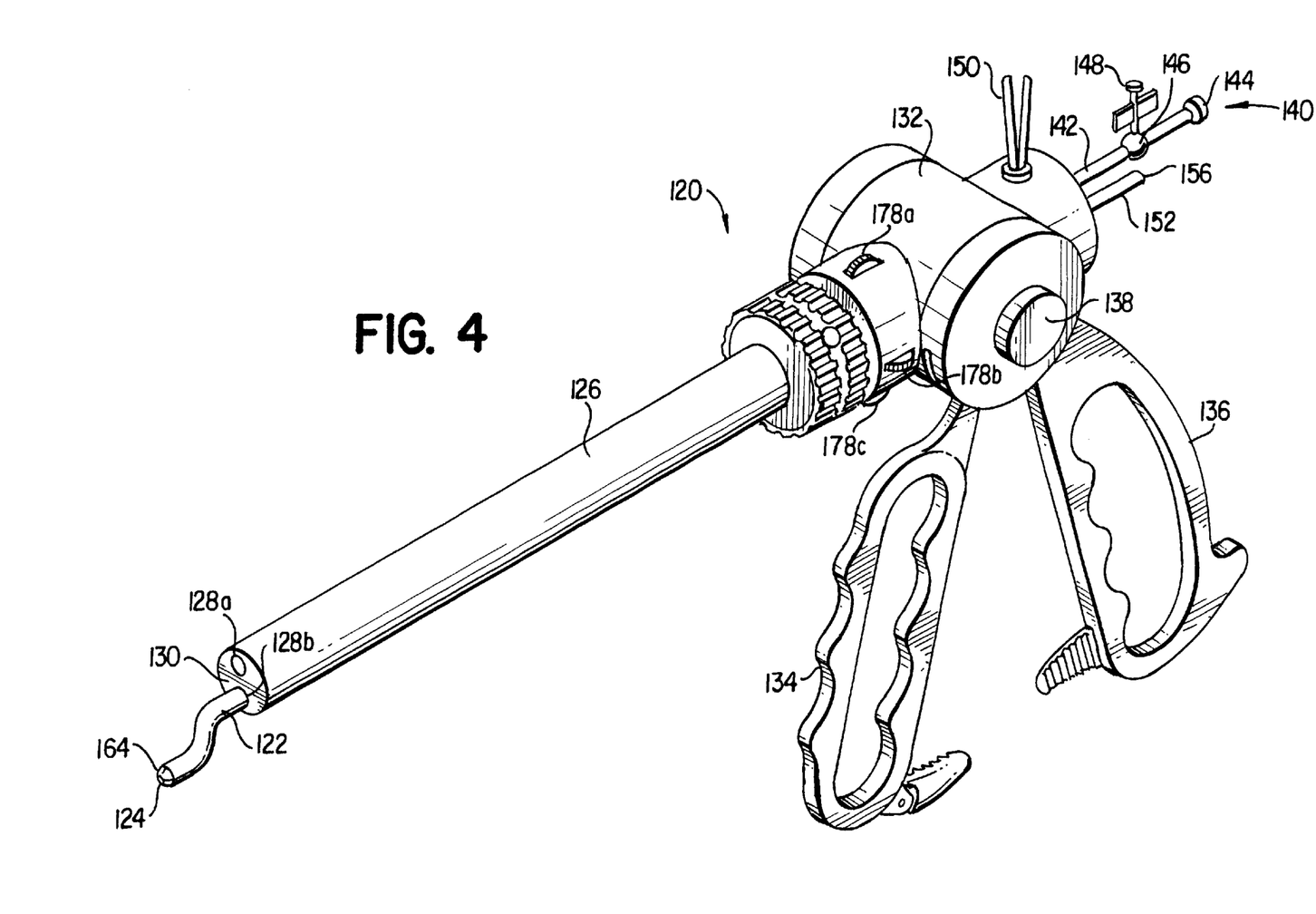
FIG. 4 is a perspective illustration of a surgical instrument having an offset endoscope with an articulable ball joint aiming mechanism.

FIG. 4 is a perspective illustration of another embodiment of a surgical instrument 120 having an offset endoscope 122 with an articulable ball joint aiming mechanism 124. Endoscopic instrument 120 includes a cylindrical barrel or outer shaft 126 having an elongated passage defined therein (preferably in the form of one or more channels, e.g., 128a and 128b), a barrel distal end 130 and a barrel proximal end terminating in a housing 132 which includes scissor type handles 134 and 136 for controlling surgical instruments, as above. Housing 132 also includes a transversely located button 138 for selectively disengaging the handles 134 and 136 and permitting rotation of the handles, thus allowing the surgeon to orient handles 134 and 136 in a desired manner before or during surgery.

The channels (e.g., 128a and 128b) in barrel 130 are lumens or passages adapted to receive elongate surgical instruments which can be inserted at the proximal ends of the channels (e.g., 140); channel 128a extends through proximal tubular body 142, which carries a Luer lock 144 and a spherical reservoir 146 for receiving a stop-cock valve 148, thereby allowing channel 128a to be sealed at the proximal end. Housing 132 includes a cautery electrode connection 150 for removable electrical connection to a source of electrical energy for cauterizing tissue using end effectors, as above.

Figures 5, 6:
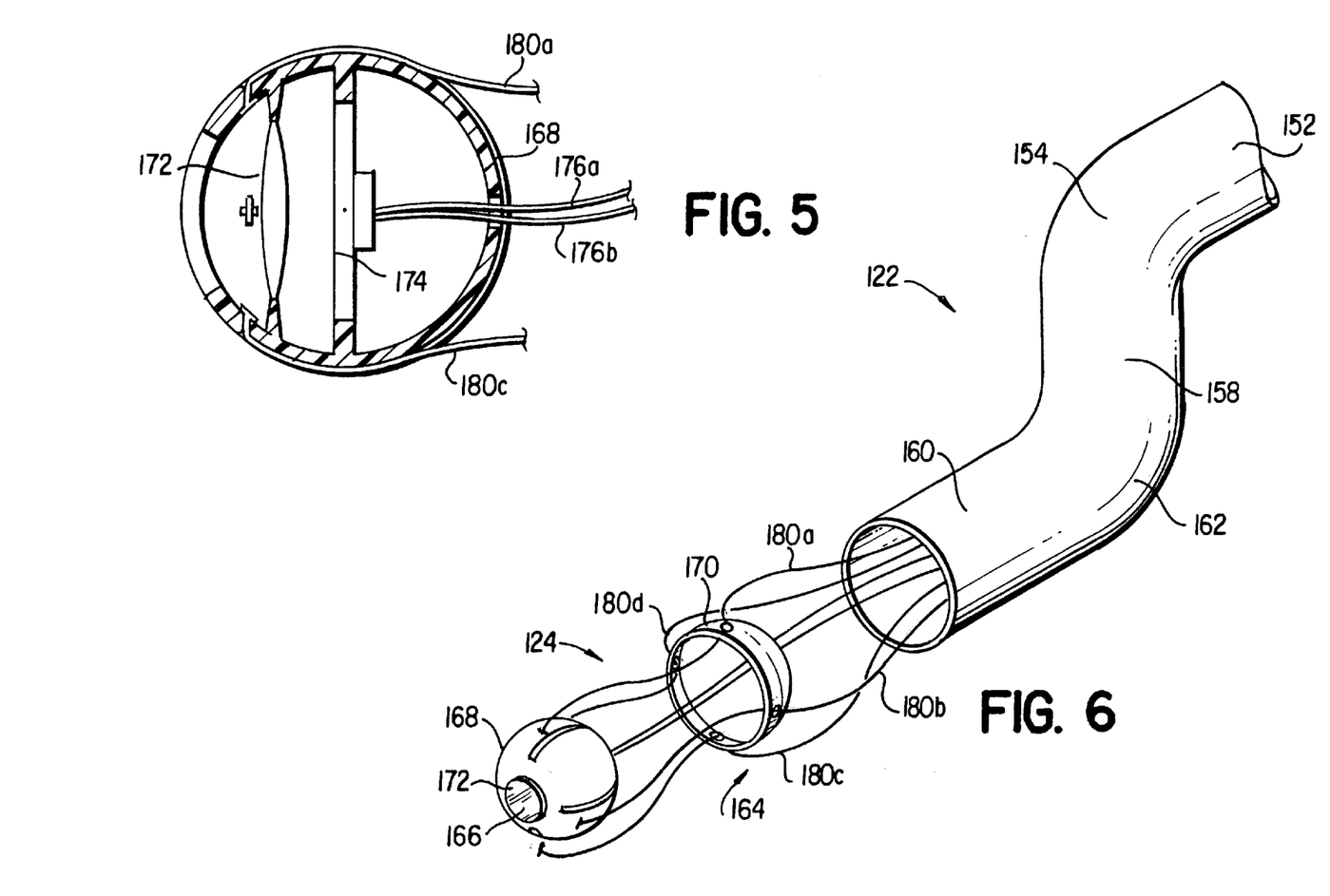
FIG. 5 is a cross sectional illustration, in elevation, of the articulable ball of the endoscope of FIG. 4.
FIG. 6 is an enlarged and exploded perspective view of the endoscope of FIG. 4.

As illustrated in FIGS. 4, 5 and 6, offset endoscope 122 has an elongate, rigid tubular body 152 with longitudinal axis and a distal end 154 opposite a proximal end 156 and is adapted to be slidably received within a barrel channel (e.g., 128b). The offset endoscope has a rigid transverse connecting member 158 rigidly connected to and extending laterally from the distal end 154, providing an offset of a selected transverse dimension. In the embodiment of FIGS. 4, 5 and 6, a longitudinally aligned distal member 160 is carried on the lateral end 162 of transverse connecting member 158 and is terminated in an articulated ball joint mechanism 124 at the endoscope distal end 164.

Articulated ball joint mechanism 124 includes an image receiving element 166 gathering light to form an image which the surgeon can interpret in performing endoscopic procedures. Image receiving element 166 can be an objective lens and/or the distal end of a fiberoptic bundle extending to the endoscope proximal end 156, as above. In the embodiment illustrated in FIGS. 5 and 6, articulated ball joint mechanism 124 includes a spherical housing 168 rotatably carried in a hemispherical socket 170 fitted within the distal tubular end of distal member 160. FIG. 5 is a cross sectional illustration, in elevation, of the articulable ball joint aiming mechanism spherical housing 168 of the endoscope 122 of FIG. 4. FIG. 6 is an enlarged and exploded perspective view of the endoscope articulated ball joint mechanism 124. Spherical housing 168 of articulated ball joint mechanism 124 includes an objective lens 172 for focusing an image on image sensor 174, preferably a CMOS or CCD solid state image sensor for converting the light from the image into an electrical image data signal transmitted proximally over wires 176a and 176b. The spherical housing 168 of articulated ball joint mechanism 124 is aimed or steered by manipulation of tension adjusting control wheels 178a, 178b, 178c, and 178d (not visible) mounted on housing 132 for selectively applying tension to control members (e.g., wires, lines, rods or cables) 180a, 180b, 180c, and 180d by rotating the control wheels with the finger. Spherical housing 168 has four equally spaced exterior grooves in the outer surface of the housing within which control lines 180a, 180b, 180c and 180d are proximally trained; the cables are faired through four apertures 182 in socket 170 and extend proximally back through the lumen in tubular endoscope body 152 to the tension adjusting control wheels 178a, 178b, 178c and 178d.

Offset endoscope 122 is slidably received in channel 128b and may be moved axially in proximal or distal directions and is rotatable therein for providing an infinite number of viewing perspectives. Offset endoscope image receiving element 166 can thus be moved radially along an arc centered on the longitudinal axis the offset endoscope rigid tubular body 152, disposed coaxially with channel 128b. An additional degree of freedom in aiming the image receiving element 166 is obtained by operation of control wheels 178a–178d for steering spherical housing 168 of articulable ball joint mechanism 124, which can aim image receiving element 166 along the longitudinal axis of distal member 160 (i.e., parallel to the longitudinal axis of barrel 126) and can aim at an oblique angle in any direction transverse to the longitudinal axis of distal member 160, thus defining a hemisphere of possible viewing angles or perspectives. Offset endoscope 122 can optionally include a light source such as an LED for illumination the field of view of image receiving element 166.

Figure 7A:
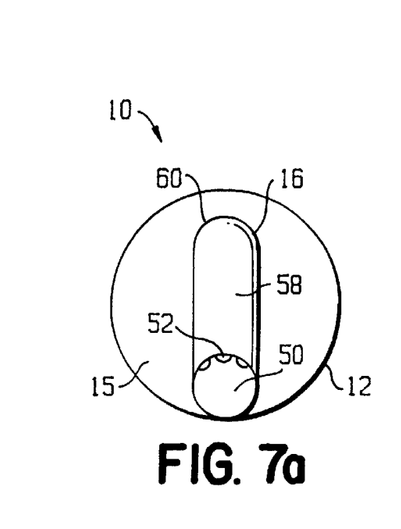
Figure 7B:
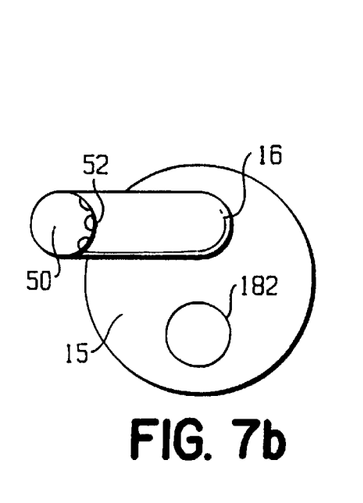
Figure 7C:
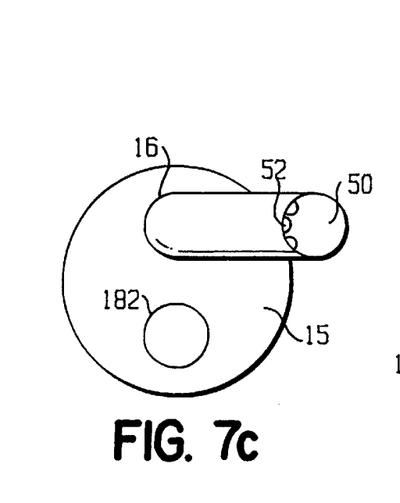
Figure 7D:
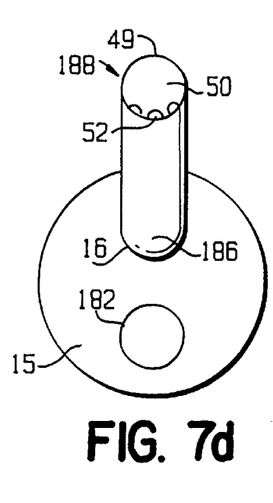
Figure 8A:
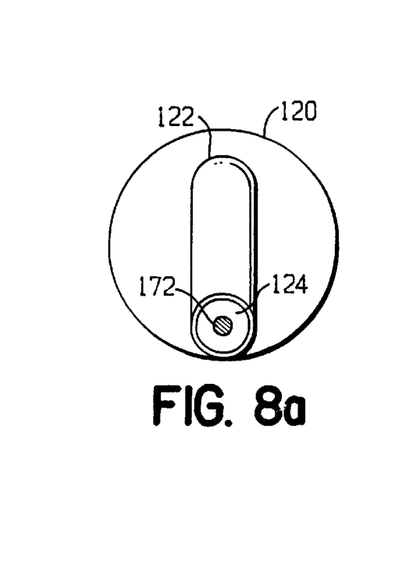
FIGS. 8a, 8b, 8c and 8d are distal end views, in elevation, illustrating the range of motion of the offset endoscope of FIG. 4.
Figure 8B:
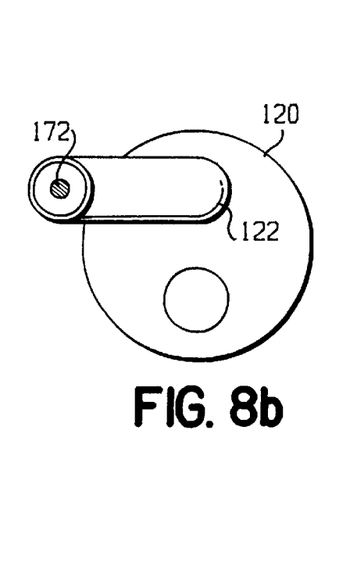
Figure 8C:
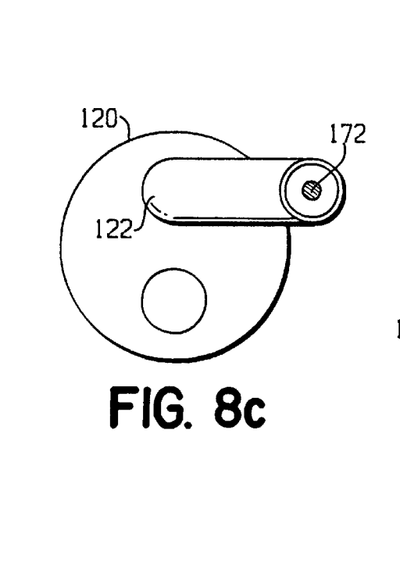
Figure 8D:
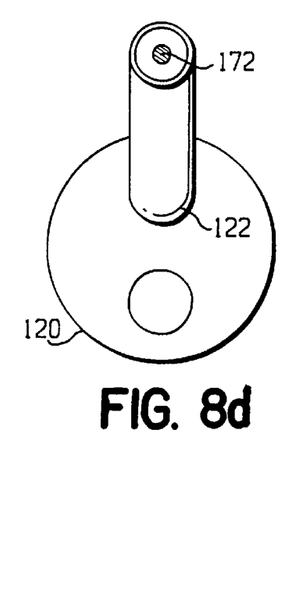

FIGS. 7a, 7b, 7c and 7d are distal end views, in elevation, illustrating the range of motion of the offset endoscope 16 of FIG. 1a. As noted above, offset endoscope 16 is slidably received in a channel of instrument barrel 12 and is rotatable therein. Offset endoscope image receiving element 52 can thus be moved radially along an arc centered on the longitudinal axis the offset endoscope rigid tubular body 60, disposed coaxially within the channel (e.g., 72c). During insertion of surgical instrument 10 within a portal sleeve (e.g, 68, not shown) offset endoscope 16 can be positioned as shown in FIG. 7a to lie within a diametrical dimension of surgical instrument barrel 12 by rotating the shaft (e.g., rotating endoscope body 60 to angularly position the viewing or distal end 50 so as to lie within a circle having the outer diameter of the barrel 12, as defined by the perimeter of barrel distal end 15). FIGS. 7b through 7d illustrate alternate rotational orientations of offset endoscope 16 having the endoscope distal end outside the diametrical dimension of instrument barrel 12. The orientations depicted in FIGS. 7a–7d illustrate four quadrants of a circular arc defined by swinging distal end 50 continuously through a circle. At each of the four positions it is noted that image receiving element 52 is aimed along the central axis of transverse connecting member 58 and so provides an oblique view directed across the barrel distal end, a view likely to provide various perspectives of the side and distal end of surgical instruments introduced through channel 182.

Referring to FIG. 7d, an alternative embodiment of offset endoscope 16 includes a first flexible knuckle joint 186 at the connection between the rigid body distal end 46 and the rigid transverse connecting member 58 and a second flexible knuckle joint 188 is provided at the connection between rigid transverse connecting member lateral end 49 and proximal end of longitudinally aligned distal member 48. The flexible knuckle joints 186 and 188 are spring biased to retain the offset endoscope shape illustrated in FIGS. 1b and 7d, but will hingedly flex to allow the offset endoscope to be aligned along the longitudinal axis of rigid tubular body 60 when the endoscope 16 is proximally withdrawn through the channel thereby bringing distal end 50 within the diametrical dimension of barrel 12. Thus, by drawing the shaft and the endoscope viewing end 50 proximally into the barrel channel (e.g., 14b), in an axial manner, the offset endoscope may be removed from instrument 10 and/or instrument 10 may be inserted into or withdrawn from a portal sleeve.

Similarly, FIGS. 8a, 8b, 8c and 8d are distal end views, in elevation, illustrating the range of motion of the offset endoscope 122 of FIG. 4 with objective lens 172 aimed along the longitudinal axis of distal member 160.

FIG. 9 is a perspective view of a surgical instrument 202 with a cylindrical barrel 204 adapted to be received within a portal sleeve 206 and having an alternative embodiment of the offset endoscope 200 including a rigid elongate body 210 with a longitudinal axis, a proximal end (not shown) and a distal end 212; the rigid elongate body 210 extends through at least a portion of barrel 204. Offset endoscope 200 also includes a rigid connecting member 214 extending distally at an oblique angle from the rigid elongate body distal end 212. An image receiving element 216 is carried upon the connecting member 214, such that the image receiving element 216 is transversely offset from the longitudinal axis of the rigid elongate body 210 of offset endoscope 200. The rigid elongate body 210 is rotatably mounted in a channel or passage within barrel 204 to move the connecting member 214 between a first position, in which image receiving element 216 is contained within a diametrical dimension of the barrel 204 (and so will pass through the lumen of tubular portal sleeve 206), and a second position (as shown in FIG. 9), in which at least a portion of the image receiving element 216 extends beyond the diametrical dimension of barrel 204. The diametrical dimension of barrel 204 is substantially equal to the inner diameter (e.g., size the lumen) of portal sleeve 206. Image receiving element 216 provides an oblique field of view 217 encompassing the side and end of surgical instrument end effector 218 introduced through another channel passage through barrel 204 of surgical instrument 202.

In as much as the present invention is subject to various modifications and changes in detail, the above description of a preferred embodiment is intended to be exemplary only and not limiting. It is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An offset rigid endoscope, comprising:
   a rigid elongate body having a longitudinal axis, a proximal end and a distal end;
   a rigid connecting member including a first connecting member portion extending at a fixed oblique angle from said rigid elongate body distal end; and
   an image receiving element carried by said connecting member, said image receiving element being offset from the longitudinal axis of said rigid elongate body and aimed along an image receiving axis angularly fixed relative to the longitudinal axis and directed towards the longitudinal axis.

2. The endoscope of claim 1, wherein said connecting member includes a second connecting member portion attached to the first connecting member portion and extending parallel to the longitudinal axis.

3. The endoscope of claim 1, further including a light source carried by said connecting member, the light source defining an oblique field of view directed towards the longitudinal axis.

4. The endoscope of claim 1, comprising:
   an elongated hollow barrel extending generally parallel to the longitudinal axis;
   wherein said rigid elongate body is slidably and rotatably mounted in said barrel, and wherein
   said rigid elongate body is mounted to rotate said connecting member between a first position in which said image receiving element is contained within a diametrical dimension of said barrel, and a second position, in which at least a portion of said image receiving element extends beyond the diametrical dimension of said barrel.

5. The instrument of claim 4, wherein said rigid elongate body is mounted in said barrel to rotate about said rigid elongate body longitudinal axis.

6. The instrument of claim 4, wherein said connecting member includes a second connecting member portion attached to the first connecting member portion and extending parallel to the longitudinal axis.

7. The instrument of claim 4, further including a light source carried by said connecting member, the light source defining an oblique field of view directed towards the longitudinal axis.

8. An offset rigid endoscope, comprising:
   a rigid elongate body having a longitudinal axis, a proximal and a distal end;
   a connecting member extending at an oblique angle from said rigid elongate body distal end; and
   an image receiving element carried by said connecting member, said image receiving element being offset from the longitudinal axis of said rigid elongate body wherein said image receiving element is carried by a moveable ball, said ball being articuable to aim said image receiving element at an oblique angle with respect to said rigid elongate body longitudinal axis.

9. A surgical endoscopic instrument for viewing anatomical tissue or other objects in a body, comprising:
   an elongated hollow barrel having a distal end and a proximal end; and
   an offset endoscope including a rigid elongate body, a connecting member and an image receiving element, the connecting member having a longitudinal axis, a proximal end and a distal end, said rigid elongate body extending through at least a portion of said barrel, the connecting member extending from said rigid elongate body distal end and the image receiving element being carried by said connecting member, said receiving element being offset from the longitudinal axis of said rigid elongate body, wherein said rigid elongate body is moveably mounted in said barrel to move said connecting member between a first position, in which said image receiving element is contained within a diametrical dimension of said barrel and a second position in which at least a portion of said image receiving element extends beyond the diametrical dimension of said barrel and wherein said image receiving element is carried by a moveable ball, said ball being articuable to aim said image receiving element at an oblique angle with respect to said rigid elongate body longitudinal axis.

10. An offset rigid endoscope, comprising:
    a rigid elongate body having a longitudinal axis, a proximal end and a distal end;
    a connecting member including a first connecting member portion extending at an oblique angle from said rigid elongate body distal end; and
    an image receiving element carried by said connecting member, said image receiving element being offset from the longitudinal axis of said rigid elongate body and aimed along an image receiving axis being positioned one of parallel to the longitudinal axis or angularly relative to and directed towards the longitudinal axis, wherein said image receiving element is carried by a movable ball, said ball being articulable to aim said image receiving element at an oblique angle with respect to said rigid elongate body longitudinal axis.

11. A surgical endoscopic instrument for viewing anatomical tissue or other objects, in a body, comprising:
    an elongated hollow barrel having a distal end and a proximal end;
    an offset endoscope including:
       a rigid elongate body having a longitudinal axis, a proximal end and a distal end, said rigid elongate body extending through at least a portion of said barrel,
       a connecting member including a first connecting member portion extending from said rigid elongate body distal end, and
       an image receiving element carried by said connecting member, said image receiving element being offset from the longitudinal axis of said rigid elongate body; and
    wherein said rigid elongate body is movably mounted in said barrel to rotate said connecting member between a first portion, in which said image receiving element is contained within a diametrical dimension of said barrel, and a second position, in which at least a portion of said image receiving element extends beyond the diametrical dimension of said barrel, and wherein said image receiving element is carried by a movable ball, said ball being articulable to aim said image receiving element at an oblique angle with respect to said rigid elongate body longitudinal axis.

12. A surgical endoscopic instrument for viewing anatomical tissue or other objects, in a body, comprising:
    an elongated hollow barrel having a distal end and a proximal end and extending along a longitudinal axis;
    an offset endoscope including:
       a rigid elongate body having a longitudinal axis, a proximal end and a distal end, said rigid elongate body extending longitudinally through at least a portion of said barrel and being disposed offset from yet parallel to the longitudinal axis,
       a connecting member including a first connecting member portion extending at a fixed oblique angle from said rigid elongate body distal end, and
       an image receiving element carried by said connecting member, said image receiving element being offset from the longitudinal axis of said rigid elongate body;
    a driver comprising a shaft having a distal end and extending longitudinally through at least a portion of said barrel, said driver carrying an end effector on said shaft distal end, the driver disposed apart from said offset endoscope and positioned one of coextensively with and offset from the longitudinal axis; and
    wherein said endoscope rigid elongate body is movably mounted in said barrel to move said connecting member between a first position, in which said image receiving element is contained within a diametrical dimension of said barrel, and a second position, in which at least a portion of said image receiving element extends beyond the diametrical dimension of said barrel.

13. The instrument of claim 12, wherein:
    said endoscope rigid elongate body is mounted in said barrel to rotate about said endoscope rigid elongate body longitudinal axis; and
    wherein said image receiving element is pointed toward said driver end effector at an oblique angle, with respect to said barrel longitudinal axis.

14. The instrument of claim 13, further including a light source carried by said connecting member.

* * * * *